(12) United States Patent
Guo et al.

(10) Patent No.: US 8,178,569 B2
(45) Date of Patent: May 15, 2012

(54) CRYSTALLINE IMIDAZOLE-5-CARBOXYLIC ACID DERIVATIVE

(75) Inventors: Jianhui Guo, Shanghai (CN); Dong An, Shanghai (CN)

(73) Assignee: Shanghai Allist Pharmaceuticals, Inc., Shanghai (CN)

( * ) Notice: Subject to any disclaimer, the term of this patent is extended or adjusted under 35 U.S.C. 154(b) by 44 days.

(21) Appl. No.: 12/682,561

(22) PCT Filed: Oct. 10, 2008

(86) PCT No.: PCT/CN2008/001715
§ 371 (c)(1),
(2), (4) Date: Jun. 16, 2010

(87) PCT Pub. No.: WO2009/049495
PCT Pub. Date: Apr. 23, 2009

(65) Prior Publication Data
US 2010/0292286 A1    Nov. 18, 2010

(30) Foreign Application Priority Data

Oct. 11, 2007  (CN) .......................... 2007 1 0094131

(51) Int. Cl.
*A61K 31/41* (2006.01)
*C07D 257/04* (2006.01)

(52) U.S. Cl. ...................................... 514/381; 548/253

(58) Field of Classification Search .................. 548/253
See application file for complete search history.

(56) References Cited

U.S. PATENT DOCUMENTS
5,298,519 A    3/1994   Binder et al.

FOREIGN PATENT DOCUMENTS

| CN | 101024643 | 8/2007 |
|---|---|---|
| EP | 1988090 A1 | 11/2008 |
| EP | 2103610 A1 | 9/2009 |
| WO | WO 2005/011646 A2 * | 2/2005 |
| WO | WO 2007/095789 A1 | 8/2007 |
| WO | WO 2008/067687 A1 | 6/2008 |

OTHER PUBLICATIONS

International Search Report and Written Opinion for corresponding PCT application No. PCT/CN2008/001715, date of mailing Jan. 22, 2009.
Harwood et al. "Experimental Organic Chemistry, Standard and Microscale", *Blackwell Science Ltd.* p. 131 (1999).
Supplementary European Search Report corresponding to European Application No. 08038798 dated Nov. 30, 2010.

* cited by examiner

*Primary Examiner* — Shawquia Young
(74) *Attorney, Agent, or Firm* — Myers Bigel Sibley & Sajovec, PA

(57) ABSTRACT

The invention provides the crystalline imidazole-5-carboxylic acid derivative (I, the chemical name: 2-butyl-4-chloro-1-[2'-(1H-tetrazol-5-yl)1,1'-biphenyl-methyl]-imidazole-5-carboxylic acid, 1-[(isopropoxy)-carbonyloxy]methyl ester), its preparation method and uses thereof.

18 Claims, 3 Drawing Sheets

CRYSTALLINE IMIDAZOLE-5-CARBOXYLIC ACID DERIVATIVE

CROSS REFERENCE TO RELATED APPLICATIONS

This application is a 35 U.S.C. §371 national phase application of PCT Application No. PCT/CN2008/001715, filed on Oct. 10, 2008, which claims priority from Chinese Patent Application 200710094131.0, filed on Oct. 11, 2007, the disclosures and contents of which are incorporated by reference herein in their entirety. The above-referenced PCT International Application was published in Chinese as International Publication No. WO2009/049495.

FIELD OF THE INVENTION

The present invention general relates to the field of drug analysis. It relates to the crystal of imidazole-5-carboxylic acid derivative (I, chemical name: 2-butyl-4-chloro-1-[2'-(1H-tetrazol-5-yl)-1,1'-biphenyl-methyl]-imidazole-5-carboxylic acid, 1-[(isopropoxy)-carbonyloxy]methyl ester), its preparation method and its use for preparing antihypertensive drugs.

BACKGROUND OF THE INVENTION

The compound of formula (I) is an Ang II receptor antagonist. Its chemical name is 2-butyl-4-chloro-1-[2'-(1H-tetrazol-5-yl)-1,1'-biphenyl-methyl]-imidazole-5-carb-oxylic acid, 1-[(isopropoxy)-carbonyloxy]methyl ester. Chinese Patent CN101024643A describes the structure, and its use as antihypertensive drugs.

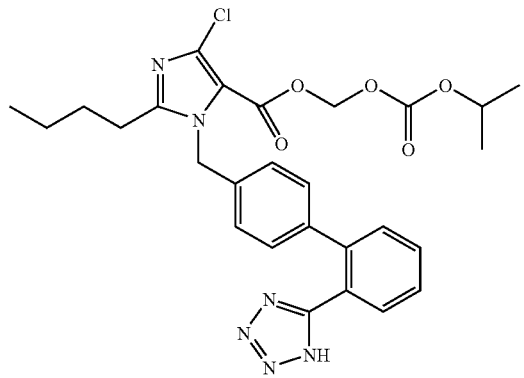

As regards to the solid physical properties of the compound of formula (I), the patent document of CN101024643A discloses that it is a white solid, and its melting point is 134.5-136° C. However, CN101024643A dose not disclose the crystalline structure of the compound of formula (I).

The crystal state of a compound may be important when the compound is used for pharmaceutical purpose. Compared with the amorphous solid, the solid physical properties of the crystalline compound may change, which may affect its whole process of pharmaceutical use. For example, the fluidity of the solid may affect the degree of difficulty of material treatment in the process of drug preparation. The powdery solid compounds with poor fluidity may not be suitable for the subsequent preparation of formulation. The solubility of the solid in water may affect the absorption, efficacy, metabolism of drugs and the preparation of liquid formulation, such as syrups. The solid form of a compound may also affect its compressive behavior and its storage stability. For example, a crystalline compound may overcome the disadvantage of an amorphous compound that it is easy to absorb moisture and metamorphose, and it has good light stability and thermal stability.

The solid physical properties mentioned above may be affected by the confirmation and orientation of the crystal cell, which may determine the specific crystal form of a substance. The crystal form mentioned has a thermodynamic behavior which differs from amorphous substance or another crystal form. The specific crystal form may be distinguished from amorphous compound or another crystal form by determining the thermal property using a melting point instrument, thermogravimetric analysis (TGA), or differential scanning calorimetry (DSC) in laboratory. Moreover, a specific crystal form has specific spectroscopic properties. For example, the specific crystal forms can be characterized by the data of powder X-ray diffraction pattern and infrared spectrum.

In addition, the preparation of crystalline compounds is one of important methods to purify the amorphous compounds in a large scale. So the crystalline compound of formula (I) and its preparation have crucial practical significance.

DETAILED DESCRIPTION

Figure 1:
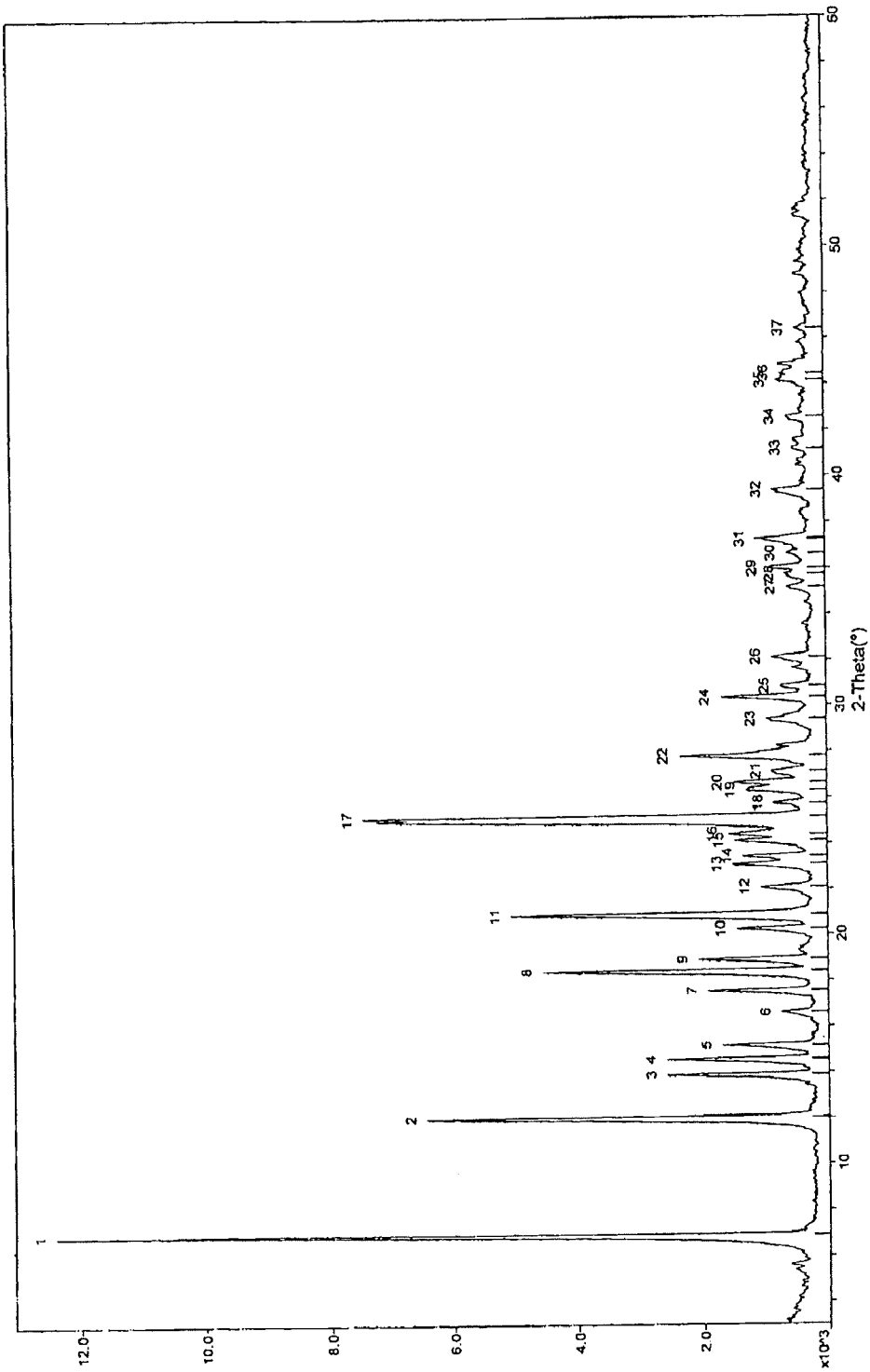
FIG. 1: powder X-ray diffraction pattern of the crystalline compound of formula (I).

The technical problem solved in the present invention is to improve the solid physical properties of the compound of formula (I), and to provide a crystalline compound of formula (I) with good fluidity and storage stability.

The present invention provides a crystalline imidazole-5-carboxylic acid derivative (I). Its chemical name is 2-butyl-4-chloro-1-[2'-(1H-tetrazol-5-yl)-1,1'-biphenyl-methyl]-imidazole-5-carboxylic acid, 1-[(isopropoxy)-carbonyloxy] methyl ester, shortly named as the crystalline compound of formula (I) in this application.

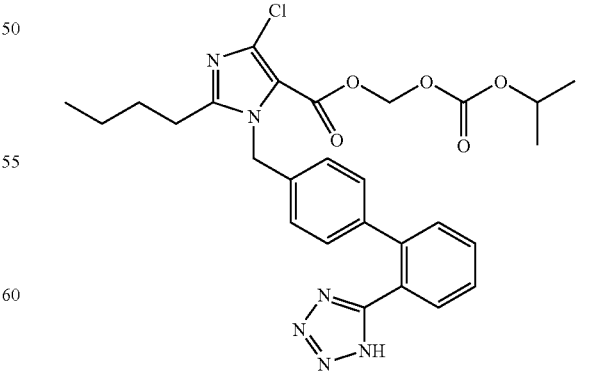

The powder X-ray diffraction pattern of the crystalline compound of formula (I) according to the present invention includes the diffraction angles 2θ (°) as follows:

High-intensity ray: 6.92±0.10, 27.14±0.10.
Moderate-intensity ray: 12.02±0.10, 13.90±0.10, 14.58±0.10, 15.18±0.10, 16.60±0.10, 17.56±0.10, 18.42±0.10, 18.94±0.10, 20.26±0.10, 20.88±0.10, 22.08±0.10, 23.10±0.10, 23.46±0.10, 24.14±0.10, 24.40±0.10, 25.16±0.10, 25.74±0.10, 26.32±0.10, 26.66±0.10, 27.80±0.10, 29.40±0.10.

The crystalline compound of formula (I) according to the present invention has the powder X-ray diffraction pattern essentially as shown in FIG. (1). Each peak is assigned as follows in Table 1:

TABLE 1

| 2θ(°) | d value (Å) | relative intensity I/I°(%) | 2θ(°) | d value (Å) | relative intensity I/I°(%) |
|---|---|---|---|---|---|
| 6.92 | 12.77 | s | 12.02 | 7.36 | m |
| 13.90 | 6.37 | m | 14.58 | 6.07 | m |
| 15.18 | 5.83 | m | 16.60 | 5.33 | m |
| 17.56 | 5.05 | m | 18.42 | 4.81 | m |
| 18.94 | 4.68 | m | 20.26 | 4.38 | m |
| 20.88 | 4.25 | m | 22.08 | 4.02 | m |
| 23.10 | 3.85 | m | 23.46 | 3.79 | m |
| 24.14 | 3.68 | m | 24.40 | 3.64 | m |
| 25.16 | 3.53 | m | 25.74 | 3.46 | m |
| 26.32 | 3.38 | m | 26.66 | 3.34 | m |
| 27.14 | 3.28 | vs | 27.80 | 3.21 | m |
| 29.40 | 3.04 | m | 30.36 | 2.94 | w |
| 30.84 | 2.90 | w | 32.12 | 2.78 | w |
| 35.18 | 2.55 | w | 35.74 | 2.51 | w |
| 36.00 | 2.49 | w | 36.64 | 2.45 | w |
| 37.28 | 2.41 | w | 39.38 | 2.29 | w |
| 41.18 | 2.19 | w | 42.56 | 2.12 | w |
| 44.16 | 2.05 | w | 44.46 | 2.04 | w |
| 46.42 | 1.95 | w | | | |

The crystalline compound of formula (I) according to the present invention has the infrared spectrum essentially as shown in FIG. (2), which includes the characteristic absorption peak listed in the following Table 2

TABLE 2

| Wavelength (cm$^{-1}$) | Transmittance (%) | Wavelength (cm$^{-1}$) | Transmittance (%) |
|---|---|---|---|
| 763 | 52 | 837 | 40 |
| 906 | 45 | 941 | 57 |
| 987 | 41 | 1020 | 67 |
| 1074 | 55 | 1136 | 52 |
| 1159 | 51 | 1256 | 71 |
| 1383 | 45 | 1410 | 43 |
| 1458 | 52 | 1483 | 47 |
| 1518 | 48 | 1732 | 71 |
| 1759 | 77 | 2871 | 41 |
| 2907 | 40 | 2934 | 42 |
| 2955 | 44 | 2987 | 43 |

The solid normal form of the crystalline compound of formula (I) according to the present invention may be needle-like, granular, massive or tabular. The melting point of the crystal is 156.0-159.0° C. determined by WRS-2A/2 microcomputer melting point instrument.

The present invention also provides a method for preparing the crystalline compound of formula (I), comprising dissolving the compound of formula (I) in a polar solvent at a temperature from 10° C. to the boiling point of the solvent, then cooling the solution to −25° C.~25° C., and allowing the solution to stand to crystallize, followed by filtering and drying to obtain the crystal of the compound of formula (I).

The present invention also provides a method for preparing the crystalline compound of formula (I), comprising dissolving the compound of formula (I) in a polar solvent at a temperature from 10° C. to the boiling point of the solvent, adding a low-polarity solvent, then cooling to −25° C.~25° C., and allowing the solution to stand to crystallize, followed by filtering and drying to obtain the crystal of the compound of formula (I). The volume ratio of the polar solvent and the low-polarity solvent mentioned is from 10:1 to 1:2.

In the method for preparing the crystalline compound of formula (I) provided in the present invention, the polar solvent mentioned is a protonic polar solvent, an aprotic polar solvent or their mixture. The protonic polar solvent is alcohol or organic acid, specifically, it may be selected from methanol, ethanol, n-propanol, isopropanol, n-butanol, isobutanol, n-pentanol, isopentanol, 2-methoxyethanol, 2-ethoxyethanol, formic acid, acetic acid, trichloroacetic acid, trifluoroacetic acid, citric acid, benzoic acid, salicylic acid, maleic acid, citric acid, or oxalic acid, preferably methanol, ethanol or isopropanol.

In the method for preparing the crystalline compound of formula (I) provided in the present invention, the aprotic polar solvent mentioned is $C_{2-6}$ ester, $C_{2-6}$ nitrile, $C_{2-6}$ ketone, $C_{2-6}$ amide, $C_{2-6}$ sulfoxide, $C_{2-6}$ sulfone, $C_{2-6}$ halogenated alkane or pyrrolidone, specifically, it may be selected from ethyl acetate, isopropyl acetate, butyl acetate, acetonitrile, propionitrile, butyronitrile, acetone, methyl isobutyl ketone, formamide, N,N-dimethylformamide, N,N-dimethylacetamide, dimethyl sulfoxide, sulfolane, N-methyl pyrrolidone or N-ethyl pyrrolidone. In some embodiments, it may be ethyl acetate, acetonitrile, dioxane or acetone.

In the method for preparing the crystalline compound of formula (I) provided in the present invention, the low-polarity solvent mentioned is $C_{3-10}$ alkane, $C_{3-10}$ cycloalkane, $C_{2-10}$ ether, or $C_{6-12}$ aromatic hydrocarbon, specifically, it may be selected from n-pentane, n-hexane, n-heptane, 2-methyl hexane, 3-methyl hexane, cyclohexane, methyl cyclohexane, ethyl cyclohexane, benzene, toluene, xylene, isopropylbenzene, 1,2,3,4-tetralin, diethyl ether, isopropyl ether, anisole, methyl-tertiarybutyl ether ethyl-tertiarybutyl ether or glycol dimethyl ether. In some embodiments, the solvent may be diethyl ether, isopropyl, n-hexane or cyclohexane.

In the method for preparing the crystalline compound of formula (I) provided in the present invention, the compound of formula (I) is obtained by removing the protective group of the compound of formula (II) in an organic solvent containing protons. The protons mentioned are provided by alcohol, water, organic acid or inorganic acid.

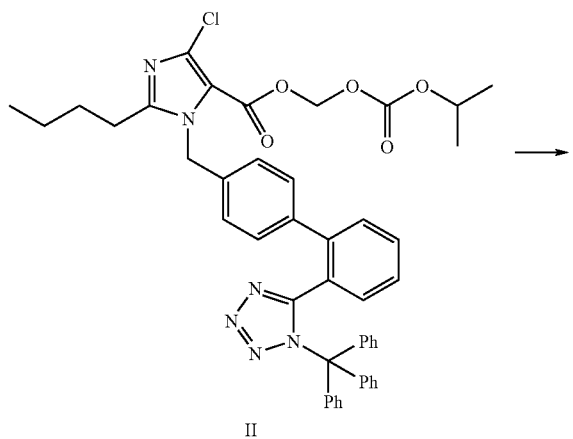

II

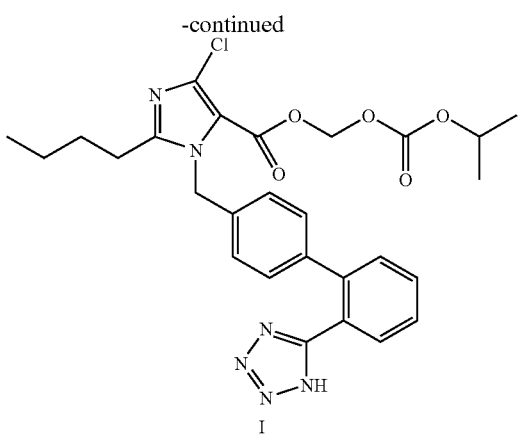

An exemplary method for preparing the crystalline compound of formula (I) is shown below. The compound of formula (II) is dissolved in ethanol, and a small amount of glacial acetic acid is added, then the mixtures is heated under reflux to remove the protective group, and the amorphous compound of formula (I) is obtained. The obtained compound is further dissolved in anhydrous ethanol under the condition of heating, then the solution is cooled to crystallize, followed by filtering and drying, and the crystalline compound of formula (I) is obtained. The crystal obtained in the above embodiment is confirmed by a powder X-ray diffraction pattern, an infrared spectrum and the melting point. Its X-ray diffraction pattern is essentially as shown in FIG. (1), and its infrared spectrum is essentially as shown in FIG. (2). The melting point of the crystal is 156.0-159.0° C. determined by WRS-2A/2 microcomputer melting point instrument. A single crystal X-ray diffraction pattern of FIG. (3) is obtained by a single crystal X-ray diffraction, which indicates that the crystal obtained in the above embodiment does not contain crystal water or crystal solvent. The size of crystal cell and the structure of crystal lattice can be calculated according to the common sense in this field.

Crystal cell parameter: a=9.9006 (13) Å, b=25.676(3) Å, c=22.378(3) Å; Crystal cell volume: V=5642.3(13) Å; the number of molecular in crystal cell is 8; Crystal density: 1,302 mg/m$^3$; Chemical formula: $C_{27}H_{29}ClN_6O_5$.

The crystalline compound of formula (I) provided in the present invention has the effect of antihypertension, and it can be administered alone or in combination with other pharmaceutically acceptable compounds. The compound can be administered to human beings orally, rectally, parenterally (intravenously, intramuscularly or subcutaneously).

Solid dosage forms for oral administration include capsules, tablets, pills, powders and granules. In such solid dosage forms, the crystalline compound of formula (I) may be mixed with at least one conventional inert excipients (or carriers) such as citrate sodium, dicalcium phosphate, or with the following components: (a) fillers or compatibilizers, for example, starch, lactose, sucrose, glucose, mannitol and silicic acid; (b) binders, for example, hydroxymethylcellulose, alginate, gelatin, polyvinylpyrrolidone, sucrose, arabic gum; (c) humectants, for example, glycerin; (d) disintegrants, for example, agar, calcium carbonate, potato starch or cassava starch, alginic acid, some composite silicate and sodium carbonate; (e) slow-dissolving agents, for example, wax, (f) absorption accelerator, for example, quaternary ammonium compound; (g) wetting agents, for example, cetyl alcohol and glycerin monostearate; (h) adsorbents, for example, kaolin; and (i) lubricants, for example, talc, calcium stearate, magnesium stearate, solid polyethylene glycol, sodium dodecyl sulfate or mixture thereof. Dosage forms such as capsules, tablets and pills may include bufferings.

Solid dosage forms, such as tablets, rotulas, capsules, pills and granules may be prepared with coatings or shells such as enteric coatings or other materials known by those skilled in the art. They can include opaque agent. Furthermore, the active compounds or compounds in the composition can be slow-released in a part of alimentary canal.

Liquid dosage forms for oral administration may include pharmaceutically acceptable emulsions, solutions, suspensions, syrups or tinctures. Besides the active compounds, the liquid dosage form may include inert diluents conventionally used in this field, such as water or other solvents, solubilizing agents and emulsifying agents, such as ethanol, isopropanol, ethyl carbonate, ethyl acetate, propylene glycol, 1,3-butanediol, dimethylformamide and oil, particularly cottonseed oil, peanut oil, corn germ oil, olive oil, caster oil and sesame oil or the mixtures of these substances. Besides the inert diluents, the composition may also include auxiliary agents such as wetting agents, emulsifying agents and suspending agents, sweetening agents, corrigents and flavors. Besides the crystalline compound of formula (I), the suspensions may include suspending agents, for example, ethoxylated isooctadecanol, polyoxyethylene sorbitol, and sorbitan ester, microcrystalline cellulose, aluminum methoxide and agar or the mixtures of these substances.

Compositions for parenteral injection may include physiologically acceptable sterile aqueous or anhydrous solutions, dispersions, suspensions or emulsions, and sterile powders for being redissolved to form sterile injection solutions or dispersions. Appropriate aqueous or anhydrous carriers, diluents, solvents or excipients include water, ethanol, polyalcohol and appropriate mixtures thereof.

When administrating the pharmaceutical composition provided by the present invention, the crystalline compound of formula (I) is applied to mammalian such as human, in a secure and effective dosage. The applied dosage is pharmaceutically acceptable effective dosage. Taking a person with weight of 60 kg for example, the daily dose is usually 1~1000 mg, preferably 20~500 mg. The specific dosage should certainly be determined in consideration of the factors, such as the route of administration and the patient's health condition.

Compared with the amorphous compound of formula (I), the crystalline compound of formula (I) provided by the present invention has a advantageous characteristic of being less hydroscopic, which rends it has good thermal stability and light stability in the process of preparation, packing, transportation and storage. In addition, the crystalline compound of formula (I) has good fluidity, which may be beneficial to the preparation of formulation. At the same time, the solubility of formula (I) is improved.

As described above, the crystalline compound of formula (I) is obtained and purified by using the difference between the solubility of the compound of formula (I) in different solvents and at different temperatures. The method described herein is simply operated, and suitable for the large scale industrial production.

In addition, in the preparation of the compound of formula (I) related in the present invention, the reaction of removing protective group can be realized by dissociation of proton from a protonic polar solvent or a little amount of protonic acid, which can largely reduce the use amount of protonic acid, and can save the cost and protect the environment.

Figure 2:
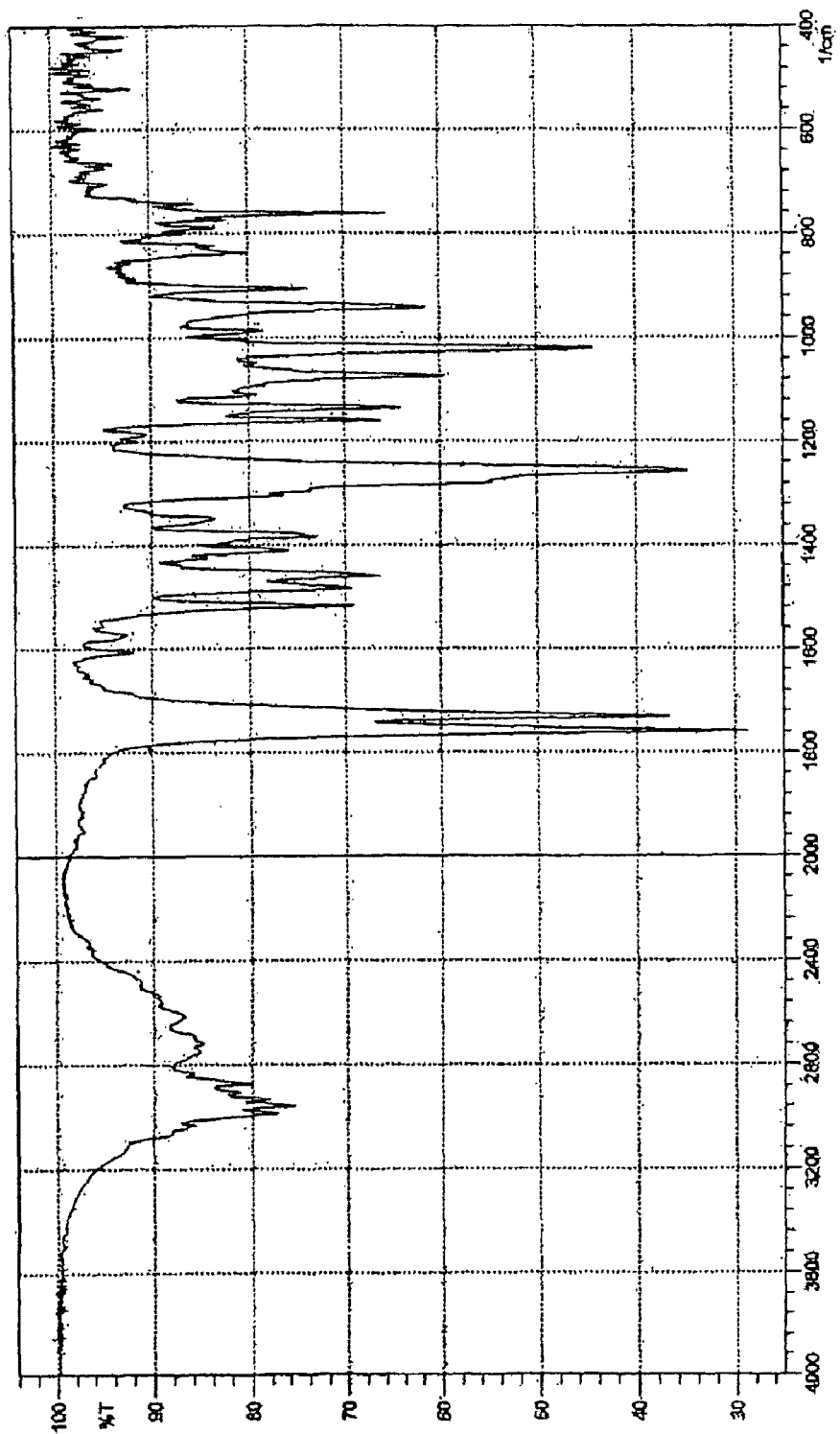
FIG. 2: infrared spectrum of the crystalline compound of formula (I).
Figure 3:
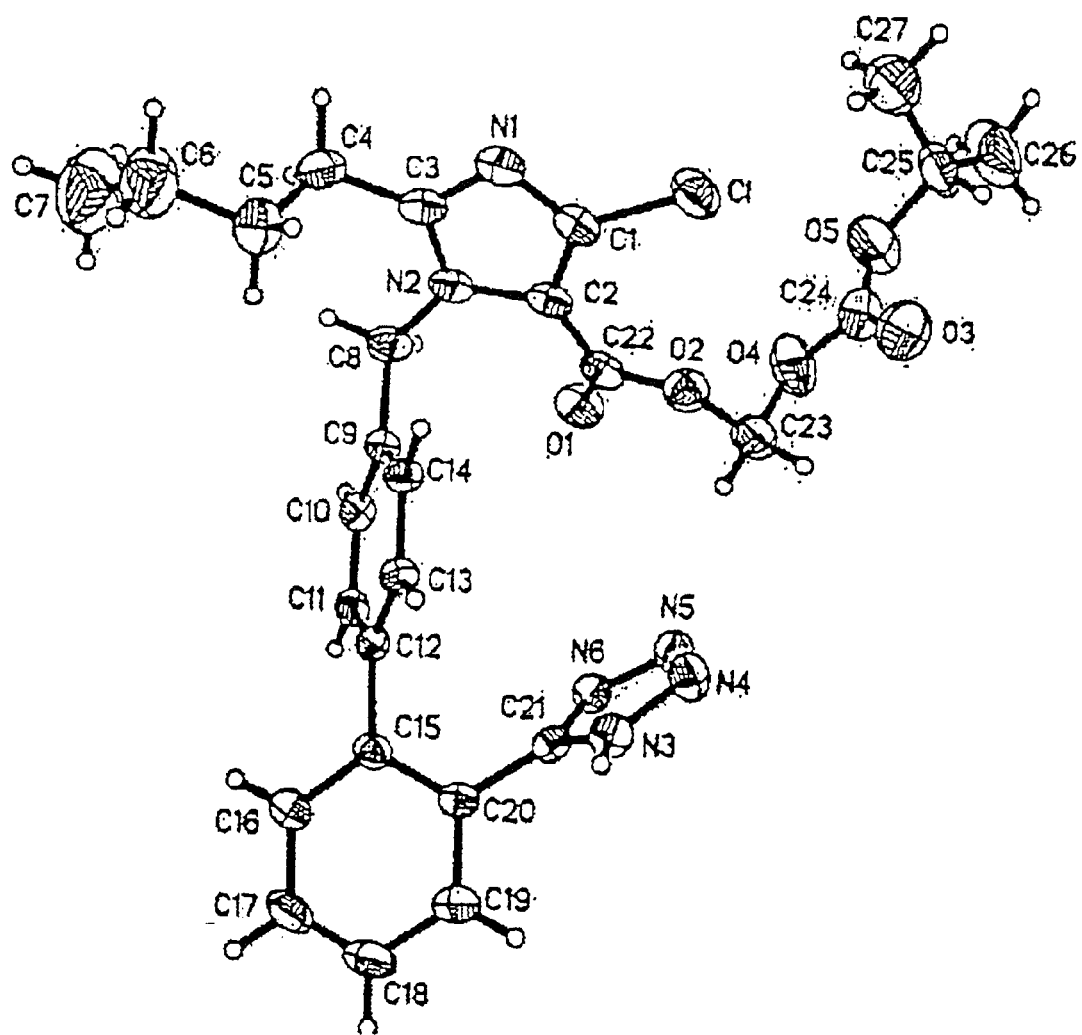
FIG. 3: single crystal X-ray diffraction pattern of the crystalline compound of formula (I).

The powder X-ray diffraction pattern of the crystalline compound of formula (I) (see FIG. 1) is measured by RIGAKUD/MNX2550VB/PC X-ray diffractometer according to the known method in the field. The infrared spectrum (see FIG. 2) is measured by KBr tablet method using FTIR-8400S infrared spectrophotometer made by Shimazu. The single crystal X-ray diffraction pattern (see FIG. 3) is measured by Smart Apex CCD diffractometer. The melting point is 156~0159.0° C., measured by WRS-2A/2 microcomputer melting point instrument.

In the powder X-ray diffraction pattern, each peak is identified by calculating according to Bragg equation. The site of each peak is determined by diffraction angle) $2\theta(°)$ and d value (Å). The classification of the intensity of peaks only reflects the approximate size of peak on each site. The definition is described in the following table:

| Relative intensity $I/I^0$ (%) | definition |
| --- | --- |
| 25~100 | Vs (very strong) |
| 10~25 | S (strong) |
| 3~10 | M (moderate) |
| 1~3 | W (weak) |

The person skilled in the art can understand that the parameters characterizing the physical properties of a crystal may have slight differences because of the errors of instruments or the difference of operators. Therefore, the above parameters can be used only for an auxiliary characterization of the crystalline compound of formula (I), and can not be regarded as a limit of the crystalline compound of formula (I) provided in the present invention.

All the literatures referred to in the present application are quoted as references, just like each literature is separately quoted as reference. It should be understood that, it will be apparent to those skilled in the art from the above disclosure that various change and modification can be made to the above embodiment based on the common knowledge or technical means in the art, and without departing from the essence of the present invention. Therefore, any equivalent alteration falls in the scope of the invention as defined in the appended claims

EXAMPLES

The present invention will be described in detail with reference to the examples. These examples are provided for illustration only, and not for the purpose of limiting the invention. The experiment methods without given the specific conditions are conducted in the conventional conditions. For example, in the drying of organic phase, it is generally washed by saturated NaCl solution, then dried by anhydrous $Na_2SO_4$.

Unless otherwise indicated, the part of solid is a weight part, the ratio of solvent is a volume ratio.

The preparation of the compound of formula (I): 2-butyl-4-chloro-1-[2'-(1H-tetrazol-5-yl)-1,1'-biphenyl-methyl]-imidazole-5-carboxylic acid, 1-[(isopropoxy)-carbonyloxy] methyl ester.

Example 1

2.10 g of 2-butyl-4-chloro-1-[2'-(1-triphenylmethyl-1H-tetrazol-5-yl)-1,1'-biphenyl-methyl]-imidazole-5-carboxylic acid, 1-[(isopropoxy)-carbonyloxy]methyl ester (2.52 mmol, purity: 95.6%, HPLC normalization method) is dissolved in 30 mL of dioxane, then added with 10 mL 4 mol/L of hydrochloric acid solution and reacted for 16 h at the room temperature. After the reaction, $NaHCO_3$ aqueous solution is added to adjust the reaction solution to pH 6 and cause the turbidity appear. The mixture is extracted with ethyl acetate. The organic phase is dried, then concentrated in reduced pressure to obtain 1.27 g white-like solid in a yield of 91.3%.

Example 2

2.10 g of 2-butyl-4-chloro-1-[2'-(1-triphenylmethyl-1H-tetrazol-5-yl)-1,1'-biphenyl-methyl]-imidazole-5-carboxylic acid, 1-[(isopropoxy)-carbonyloxy]methyl ester (2.52 mmol, purity: 95.6%, HPLC normalization method) is dissolved in 20 ml of THF, then added with 6 ml of glacial acetic acid and reacted for 16 h at the room temperature. After the reaction, $NaHCO_3$ aqueous solution is added to adjust the reaction solution to pH 6 and cause the turbidity appear. The mixture is extracted with ethyl acetate. The organic phase is dried, then concentrated in reduced pressure to obtain 1.27 g white-like solid in a yield of 91.3%.

Example 3

4.10 g of 2-butyl-4-chloro-1-[2'-(1-triphenylmethyl-1H-tetrazol-5-yl)-1,1'-biphenyl-methyl]-imidazole-5-carboxylic acid, 1-[(isopropoxy)-carbonyloxy]methyl ester (4.93 mmol, purity: 95.6%, HPLC normalization method) is dissolved in 50 ml of ethanol, then added with 0.85 ml of glacial acetic acid, heated to reflux and reacted for 10 h. After the reaction, stopping heating, the solution is cooled naturally to the room temperature (24° C.). A plenty of solid is precipitated, and filtered. The filtrate is concentrated in reduced pressure to dryness, and 2.48 g white solid is obtained in a yield of 92.7%.

The preparation of the crystalline compound of formula (I)

Example 4

1.27 g of the compound of formula (I), added with 10 ml of ethyl acetate, is dissolved by stirring and heating to 60° C. The solution is added with 5 ml of n-hexane, then cooled slowly to 0° C., suction filtered, dried to obtain 0.86 g of crystal in a yield of 64.0%.

Example 5

1.27 g of the compound of formula (I), added with 10 ml of ethyl acetate, is dissolved by stirring and heating to 60° C.

The solution is added with 5 ml of cyclohexane, then cooled slowly to 0° C., suction filtrated, dried to obtain 0.70 g of crystal in a yield of 52.3%.

Example 6

2.48 g of the compound of formula (I), added with 18 ml of ethyl acetate, is dissolved by stirring and heating to 60° C. The solution is cooled slowly to 0° C., filtrated, dried to obtain 1.86 g of white needle-like crystal in a yield of 72.5%.

Example 7

2.00 g of the compound of formula (I), added with 7 ml of anhydrous ethanol, is dissolved by stirring and heating to reflux, then cooled slowly to 0° C., dried to obtain clustered needle-like crystal in a yield of 85.0%.

Example 8

2.00 g of the compound of formula (I), added with 10 ml of isopropanol, is dissolved by stirring and heating to reflux, then cooled slowly to 0° C., dried to obtain clustered needle-like crystal in a yield of 85.0%.

Example 9

2.00 g of the compound of formula (I), added with 8 ml of acetonitrile, is dissolved by stirring and heating to 60° C., then cooled slowly to 0° C., dried to obtain granular crystal in a yield of 72.5%.

Example 10

1.00 g of the compound of formula (I), added with 7 ml of anhydrous methanol, is dissolved by stirring and heating to 60° C. Then 30 ml of isopropyl ether is added. The solution is cooled to the room temperature, filtered, and dried to obtain tabular crystal in a yield of 58.2%.

Example 11

2.00 g of the compound of formula (I), added with 10 ml of dioxane, is dissolved by stirring and heating to 60° C., then cooled to the room temperature, filtered, and dried to obtain tabular crystal in a yield of 55.3%.

Example 12

5.00 g of the compound of formula (I), added with 30 ml of acetone, is dissolved by stirring and heating to reflux, then cooled to 0° C., filtered, and dried to obtain needle-like crystal in a yield of 31.7%.

Example 13

The powder X-ray diffraction pattern of each crystal obtained in Examples 4-12 is measured by RIGAKUD/MNX2550VB/PC X-ray diffractometer.

The condition of measurement: The initial furnace temperature is 150° C.; The rate of heating is 0.5° C./min; Parallel measurement is conducted for three times; The powder X-ray diffraction pattern of FIG. (1) is obtained.

Example 14

The infrared spectrum of each crystal obtained in Examples 4-12 is measured by KBr tablet method using FTIR-8400S infrared spectrophotometer made by Shimazu.

The condition of measurement: about 3 mg of each crystal obtained in Example 4-12 is put into an agate mortar, then added with 100 mg of dried potassium bromide, grinded fully and uniformly. The mixture is then transferred to a compression mould with a diameter of 13 mm, spread evenly and pressed to 7 t·cm$^{-1}$ for a moment. The prepared test sample is taken out, confirmed to be even by eye-view, and put in the optical path of the instrument. The spectrogram is read and the infrared spectrum essentially as shown in FIG. (2) is obtained.

Example 15

The melting point of each crystal obtained in Example 4-12 is determined by WRS-2A/2 microcomputer melting point instrument.

The condition of measurement: The initial furnace temperature is 150° C. The rate of heating is 0.5° C./min. Parallel measurement is conducted for three times. The scope of melting point measured is 156.0-159.0° C.

Example 16

The single crystal X-ray diffraction pattern of the crystal obtained in Example 7 is determined by Smart Apex CCD diffractometer.

The condition of measurement: Target: Copper target; Tube voltage: 40 kv; Tube current: 100 mA. The initial angle: 3°. The terminal angle: 60°. The step length: 0.02. The slit: 2/4/0.5/0.2. The single crystal X-ray diffraction pattern essentially as shown in FIG. (3) is obtained.

Example 17

Pharmaceutical Composition

Crystalline compound of formula (I) 23 g

Starch 140 g

Microcrystalline cellulose 67 g

The above substances are mixed uniformly, and filled into common gelatine capsules to obtain 1000 capsules according to the conventional methods.

The invention claimed is:

1. A crystal form of a compound of formula (I),

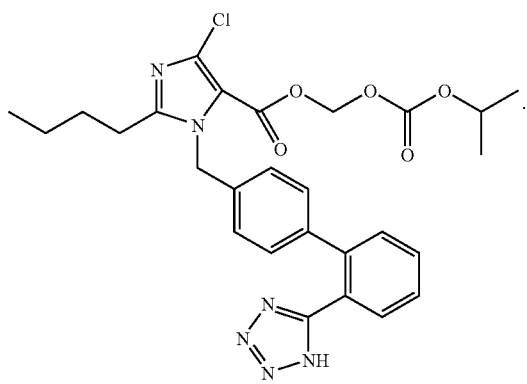

2. The crystal form according to claim 1 having an X-ray powder diffraction pattern comprising characteristic peaks expressed in the diffraction angles 2θ (°) at about
strong intensity: 6.92 and 27.14, and
medium intensity: 12.02, 13.90, 14.58, 15.18, 16.60, 17.56, 18.42, 18.94, 20.26, 20.88, 22.08, 23.10, 23.46, 24.14, 24.40, 25.16, 25.74, 26.32, 26.66, 27.80 and 29.40.

3. The crystal form according to claim 1 having an X-ray powder diffraction pattern as shown in FIG. (1).

4. A method of preparing a crystal form of a compound of formula I,

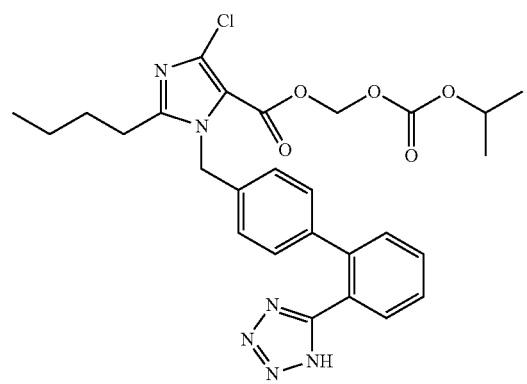

comprising:
dissolving the compound of formula (I) in a polar solvent at a temperature in a range of about 10° C. to the boiling point of the solvent,
cooling the solution to a temperature in a range of about −25° C.~25° C., and precipitating the crystal of the compound of formula (I).

5. The method of claim 4, wherein the crystal form of formula I exhibits an X-ray powder diffraction pattern comprising characteristic peaks expressed in the diffraction angles 2θ (°) at about
strong intensity: 6.92 and 27.14, and
medium intensity: 12.02, 13.90, 14.58, 15.18, 16.60, 17.56, 18.42, 18.94, 20.26, 20.88, 22.08, 23.10, 23.46, 24.14, 24.40, 25.16, 25.74, 26.32, 26.66, 27.80 and 29.40.

6. The method according to claim 4, wherein the polar solvent is a protonic polar solvent, an aprotic polar solvent or a combination thereof.

7. The method according to claim 6, wherein the protonic polar solvent is an alcohol or an organic acid.

8. The method according to claim 7, wherein the protonic polar solvent is selected from the group consisting of methanol, ethanol, n-propanol, isopropanol, n-butanol, isobutanol, pentanol, isopentanol, 2-methoxyethanol, 2-ethoxyethanol, formic acid, acetic acid, trichloroacetic acid, trifluoroacetic acid, citric acid, benzoic acid, salicylic acid, maleic acid, citric acid and oxalic acid.

9. The method according to claim 6, wherein the aprotic polar solvent is selected from the group consisting of $C_{2-6}$ ester, $C_{2-6}$ nitrile, $C_{2-6}$ ketone, $C_{2-6}$ amide, $C_{2-6}$ sulfoxide, $C_{2-6}$ sulfone, $C_{2-6}$ halogenated alkane and pyrrolidone.

10. The method according to claim 6, wherein the aprotic polar solvent is selected from the group consisting of ethyl acetate, isopropyl acetate, butyl acetate, acetonitrile, propionitrile, butyronitrile, acetone, methyl isobutyl ketone, formamide, N,N-dimethylformamide, N,N-dimethylacetamide, dimethyl sulfoxide, sulfolane, N-methyl pyrrolidone and N-ethyl pyrrolidone.

11. The method of claim 4 further comprising adding a low polarity solvent after dissolving the compound of formula (I) in a polar solvent, and wherein the volume ratio of the polar solvent and the low polarity solvent is in a range of about 10:1 to 1:2.

12. The method according to claim 11, wherein the low-polarity solvent is selected from the group consisting of $C_{3-10}$ alkane, $C_{3-10}$ cycloalkane, $C_{2-10}$ ether, and $C_{6-10}$ aromatic hydrocarbon.

13. The method according to claim 11, wherein the low polarity solvent is selected from the group consisting of n-pentane, n-hexane, n-heptane, 2-methyl hexane, 3-methyl hexane, cyclohexane, methyl cyclohexane, ethyl cyclohexane, benzene, toluene, xylene, isopropylbenzene, 1,2,3,4-tetralin, diethyl ether, isopropyl ether, anisole, methyl-tertiarybutyl ether, ethyl-tertiarybutyl ether and glycol dimethyl ether.

14. The method according to claim 4 further comprising obtaining the compound of formula (I) by removing the protection group of the compound of formula (II) using an organic solvent containing protons, wherein the protons are provided by an alcohol, water, organic acid or an inorganic acid,

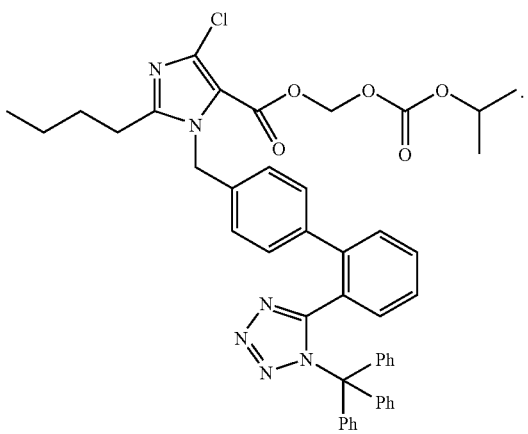

15. A pharmaceutical composition comprising a crystal form of a compound of formula (I),

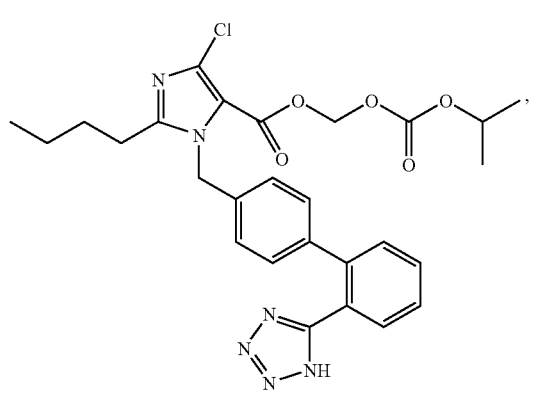

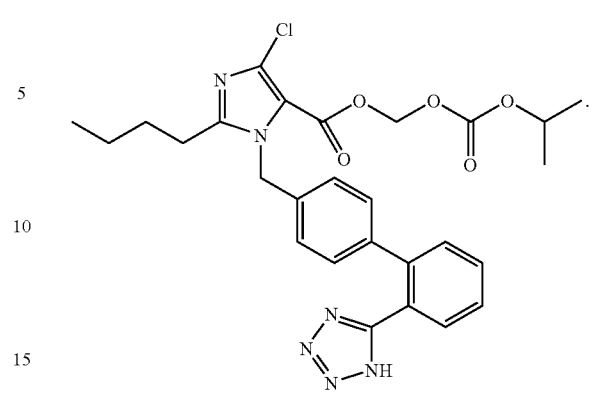

and a pharmaceutically acceptable carrier.

16. The composition of claim 15, wherein the crystal form exhibits an X-ray powder diffraction pattern comprising characteristic peaks expressed in the diffraction angles 2θ (°) at about
strong intensity: 6.92 and 27.14, and
medium intensity: 12.02, 13.90, 14.58, 15.18, 16.60, 17.56, 18.42, 18.94, 20.26, 20.88, 22.08, 23.10, 23.46, 24.14, 24.40; 25.16, 25.74, 26.32, 26.66, 27.80 and 29.40.

17. A method of treating hypertension comprising administering a therapeutically effective amount of a crystal form of a compound of formula (I), 18. The method according to claim 17, wherein the crystal form of the compound of formula (I) exhibits an X-ray powder diffraction pattern comprising characteristic peaks expressed in the diffraction angles 2θ (°) at about
strong intensity: 6.92 and 27.14, and
medium intensity: 12.02, 13.90, 14.58, 15.18, 16.60, 17.56, 18.42, 18.94, 20.26, 20.88, 22.08, 23.10, 23.46, 24.14, 24.40, 25.16, 25.74, 26.32, 26.66, 27.80 and 29.40.

* * * * *

UNITED STATES PATENT AND TRADEMARK OFFICE
CERTIFICATE OF CORRECTION

PATENT NO. : 8,178,569 B2
APPLICATION NO. : 12/682561
DATED : May 15, 2012
INVENTOR(S) : Guo et al.

Page 1 of 1

It is certified that error appears in the above-identified patent and that said Letters Patent is hereby corrected as shown below:

In the Patent:

Column 3, Table 1; Please replace table headers as follows:
Table 1

| $2\theta(°)$ | d value (Å) | relative intensity $I/I^0(\%)$ | $2\theta(°)$ | d value (Å) | relative intensity $I/I^0(\%)$ |
|---|---|---|---|---|---|
| | | | | | |

Column 7, Line 20: Please correct "is 156~0159.0° C.,"
to read -- is 156.0~159.0 °C, --

Line 24: Please correct "diffraction angle) 20(°)"
to read -- diffraction angle 20($^0$) --

Signed and Sealed this
Fifth Day of February, 2013

Teresa Stanek Rea
*Acting Director of the United States Patent and Trademark Office*